United States Patent
Carroll et al.

(10) Patent No.: US 6,937,905 B2
(45) Date of Patent: Aug. 30, 2005

(54) OSTEOGENESIS STIMULATOR WITH DIGITAL SIGNAL PROCESSING

(75) Inventors: William J. Carroll, La Center, WA (US); Michael B. McGraw, Vancouver, WA (US); William A. Rux, Hillsboro, OR (US)

(73) Assignee: International Rehabilitative Coion Sciences, Inc., Vancouver, WA (US)

( * ) Notice: Subject to any disclaimer, the term of this patent is extended or adjusted under 35 U.S.C. 154(b) by 0 days.

(21) Appl. No.: 10/631,968

(22) Filed: Aug. 1, 2003

(65) Prior Publication Data

US 2004/0059394 A1 Mar. 25, 2004

Related U.S. Application Data

(60) Provisional application No. 60/400,066, filed on Aug. 2, 2002.

(51) Int. Cl.[7] .............................. A61N 1/18; A61N 1/32
(52) U.S. Cl. .............................. 607/51; 607/50; 607/67
(58) Field of Search ........................ 607/50–51, 66–69

(56) References Cited

U.S. PATENT DOCUMENTS

| 6,560,487 B1 | * | 5/2003 | McGraw et al. | ............... 607/51 |
| 6,584,358 B2 | * | 6/2003 | Carter et al. | ................... 607/69 |
| 2002/0099425 A1 | * | 7/2002 | Johnson et al. | ............... 607/67 |

* cited by examiner

Primary Examiner—Carl Layno
(74) Attorney, Agent, or Firm—Blank Rome LLP

(57) ABSTRACT

A stimulator and a method for electrical stimulation of bone to promote osteogenesis is disclosed in which surface electrodes positioned around an incision site transmit an interferential current that has a base medium frequency alternating current between 1K–20 KHz. A digital signal processor generates a sine-wave-like waveform from a pulse generator which after further processing is used to generate two circuits for use in producing the interferential current. The effective area of stimulation is controlled by placement of electrodes and electrode orientation. Amplitude modulation of electrical circuits created at the electrode placements also augments the effective area of stimulation.

10 Claims, 2 Drawing Sheets

OSTEOGENESIS STIMULATOR WITH DIGITAL SIGNAL PROCESSING

REFERENCE TO RELATED APPLICATION

The present application claims the benefit of U.S. Provisional Patent Application No. 60/400,066, filed Aug. 2, 2002, whose disclosure is hereby incorporated by reference in its entirety into the present disclosure.

FIELD OF THE INVENTION

The present invention is generally related to osteogenesis and, more particularly, is related to an apparatus and method for the electrical stimulation of bone to promote osteogenesis, and aids in the treatment of osteoporosis.

BACKGROUND OF THE INVENTION

Spinal fusion surgery in the clinical setting has a reported failure (non union) rate of anywhere from 5% to 35%. While many variables are thought to affect the success rate of spine fusion procedures, most attempts to improve the clinical outcome have focused on internal or external fixation techniques that augment the biomechanical stability of the fusion mass. More recently, however, pre-clinical investigations have sought to understand the role and importance of biological and physical factors in the healing and subsequent stabilization of the fusion mass. Electrical stimulation in various forms has been demonstrated to improve the overall fusion rate in clinical populations.

However, current technology uses electrical leads that are implanted in the bony fusion mass, which must be left behind during explantation of the battery cell. Also, patient compliance is an issue with the current techniques employed in clinically attachable bone growth surface electrode stimulators.

Thus, a heretofore unaddressed need exists in the industry to address the aforementioned deficiencies and inadequacies.

SUMMARY OF THE INVENTION

Embodiments of the present invention provide an apparatus and method for osteogenesis and the treatment of osteoporosis using electrical stimulation of the bone. The present invention utilizes an interferential current that has a base medium frequency alternating current between 1 KHz and 20 KHz. An interferential current is set up between two circuits that are arranged in a cross-pattern on the subject's targeted area of stimulation. Where the circuits superimpose in a cross-pattern, the resultant beat frequency will be the difference between the frequencies of the two circuits and will usually range between 0–250 Hz and can be dynamic, and the amplitude will be additive and greater than either circuit alone. Multiple levels of spinal fusion can be treated depending upon the electrode placement and modulation pattern selected. The amplitudes of the outputs in the respective circuits may be modulated to increase the area of targeted stimulation. Interferential current allows improved directional control and depth of penetration in comparison to other standard osteogenesis stimulators.

Briefly described, in architecture, one embodiment of the invention, among others, can be implemented as follows.

Digital signal processors (DSPs) are used for improving the accuracy and reliability of digital signals that are used extensively in the communications field. Digital signal processing works by standardizing or clarifying the output of a digital signal. In this embodiment, the digital signal processor is used to shape multiple pulsatile waveforms to approximate the output of a sine-wave generator. In another embodiment of the invention, the digital signal processor is replaced with a field-programmable gate array (FPGA). An FPGA is an integrated circuit that can be programmed in the field after it is manufactured and therefore allows users to adjust the circuit output as the needs change. Both the DSP and the FPGA process a digital signal into a pseudo-sine-wave current waveform from the digital pulses generated by a pulse generator. The pseudo-sine-wave current waveform is transmitted through surface electrodes at a targeted area creating an interferential current. That interferential current is used for osteogenesis.

Embodiments of the present invention can also be used to provide methods for electrical stimulation of bone to promote osteogenesis. In that regard, one embodiment of such a method, among others, can be broadly summarized by the following procedure:

A first and second pair of surface electrodes are positioned on a subject's skin surface at a targeted area. A digital signal processor (or a field-programmable gate array) is connected to the surface electrodes. A pulse generator is connected to the digital signal processor and generates digital pulses. The digital signal processor processes the digital pulses to approximate the output of a sine-wave generator (pseudo-sine-wave output). The processed pseudo-sine-wave is transmitted to the surface electrodes wherein an interferential current is produced and generated at the targeted area. The interferential current is used for osteogenesis and the treatment of osteoporosis.

Preliminary studies have shown that the DSP pseudo-sine-wave interferential current produces a significantly higher level of bone growth and in particular, increased secondary or lamellar bone growth. The DSP generates individual pulses of differing widths. When those differing width pulses are driven into a transformer, they produce an output that simulates a sine wave (hence the term pseudo-sine-wave, or sine-wave-like waveform). That pseudo-sine-wave produces a "ringing" effect and harmonics are formed due to the interaction of the pulses. The waveform that is generated looks "fuzzy" in comparison to a waveform that is generated by a standard true sine-wave generator and it is believed that that harmonic 'ringing' has a superior effect on the osteoblastic activity.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

A preferred embodiment of the invention and modifications thereof will now be described with reference to the drawings.

Figure 1:
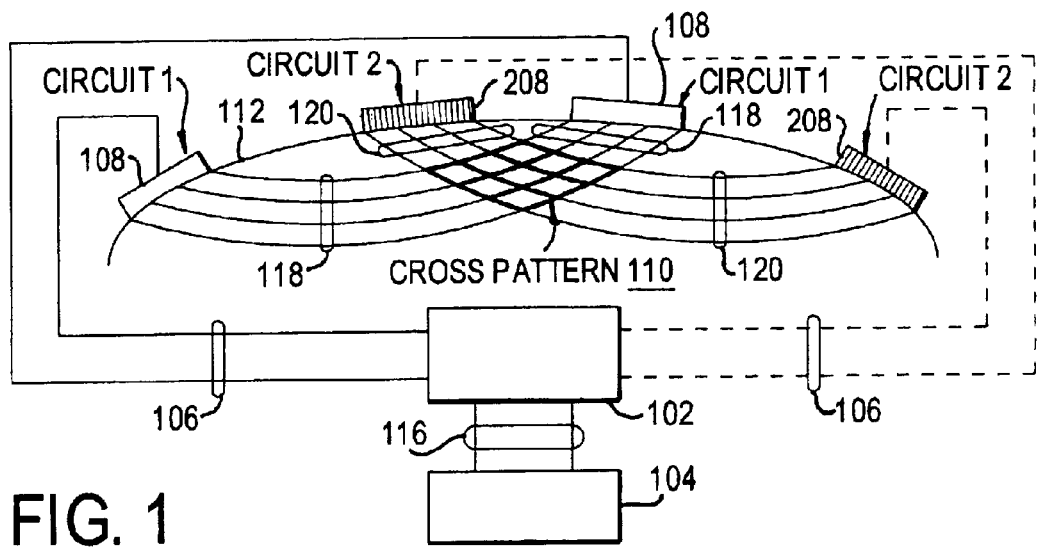
FIG. 1 is a perspective view of an interferential current set up by two circuits that are arranged in a cross pattern.
Figure 2:
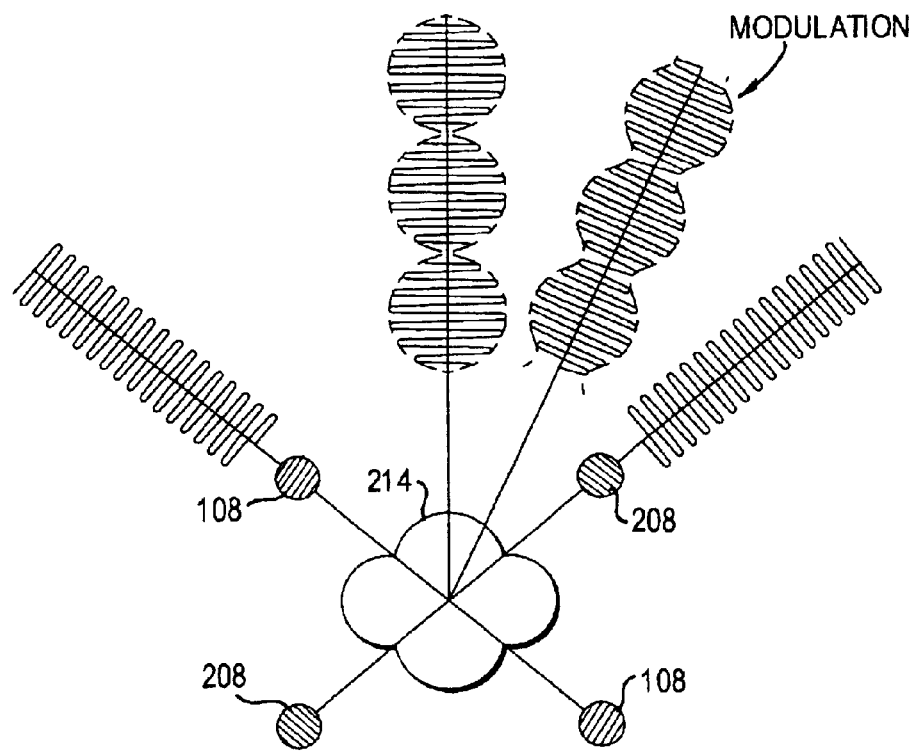
FIG. 2 is a perspective view of an interferential current pattern indicating the current intensity level and area of beat frequency formation.

FIG. 1 shows a stimulator 100 for the electrical stimulation of bone to promote osteogenesis utilizing an interferential current 110 that has a base medium frequency alternating current between 1K–20 KHz. The interferential current 110 is set up between two circuits 118, 120 that are arranged in a cross-pattern. A first pair of surface electrodes 108, 208 are positioned on a subject's skin surface 112 at one set of diagonal corners of a targeted area 214 (see FIG. 2). A second pair of surface electrodes 108, 208 is then positioned at the other set of diagonal corners of the targeted area 214. A digital signal processor 102 is connected to the first and second pairs of surface electrodes 108. When a signal generating source 104 is connected to the digital signal processor 102, a sine-wave-like waveform signal output 106 is created. The results indicate that currents produced by surface interferential stimulation has positive effects on the tensile strength and the formation of mineralized surface area at fusion sites. The fibrous connective tissue formed between autograft fragments promotes the biomechanical properties of the fusion mass. The digital signal processor 102 improves the accuracy and reliability of digital signals. The digital signal processor 102 processes the multiple pulses 116 from the signal generating source 104 to approximate a sine-wave (pseudo-sine-wave or sine-wave-like). The digital signal processor 102 generates individual pulses 106 of differing widths and resultant amplitudes. When those differing pulses 106 are driven into a transformer (not shown), the pseudo-sine-wave is produced. A pulse generator 104 is connected to the digital signal processor 102 and supplies a pulsed digital signal output 116 to the digital signal processor 102. The digital signal 106 processed by the digital signal processor 102 creates a first circuit 118 and a second circuit 120 at the first and second pairs of surface electrodes 108, 208, respectively. Where the first and second circuits 118, 120 superimpose, the resultant beat frequency (which is preferably between 1 and 250 beats/second) will be the difference between the frequencies of the two circuits, and the amplitude will be additive and greater than either circuit alone (FIG. 2).

Figure 3:
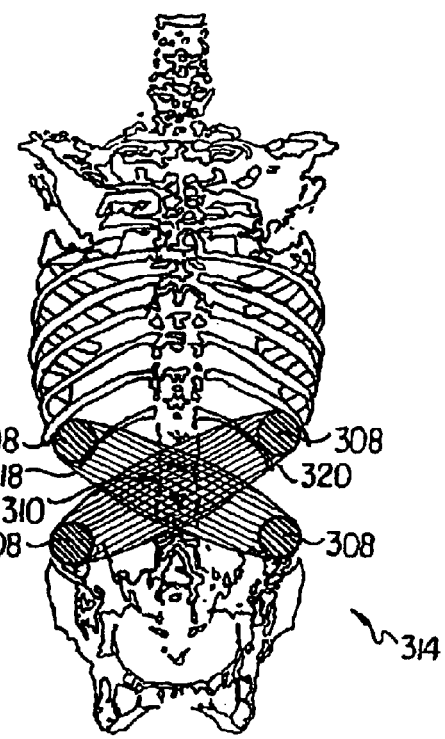
FIG. 3 is a perspective view illustrating the effective area of stimulation resulting from the crossing of separate circuits.

Multiple levels of spinal fusion can be treated depending on the placement of the first and second pairs of electrodes 308 and by modulating the amplitudes of the outputs of the first and second circuits 318, 320 (see FIG. 3). Modulating the outputs of the first and second circuits 318, 320 increases the area of the targeted stimulation. The depth of modulation can vary from 0 to 100% and depends on the direction of the currents established by the first and second circuits 318, 320. When the first and second circuits 318, 320 intersect at 90°, the maximum resultant amplitude and the deepest level of modulation is half-way between the two circuits (45° diagonally). (See FIG. 2). Thus, also, the number of vertebral segments stimulated can be controlled by the placement of the first and second pairs of electrodes 308 and their spatial orientation as described above. The area of stimulation can be augmented by modulation of the amplitudes of the outputs of the two circuits.

Figure 4:
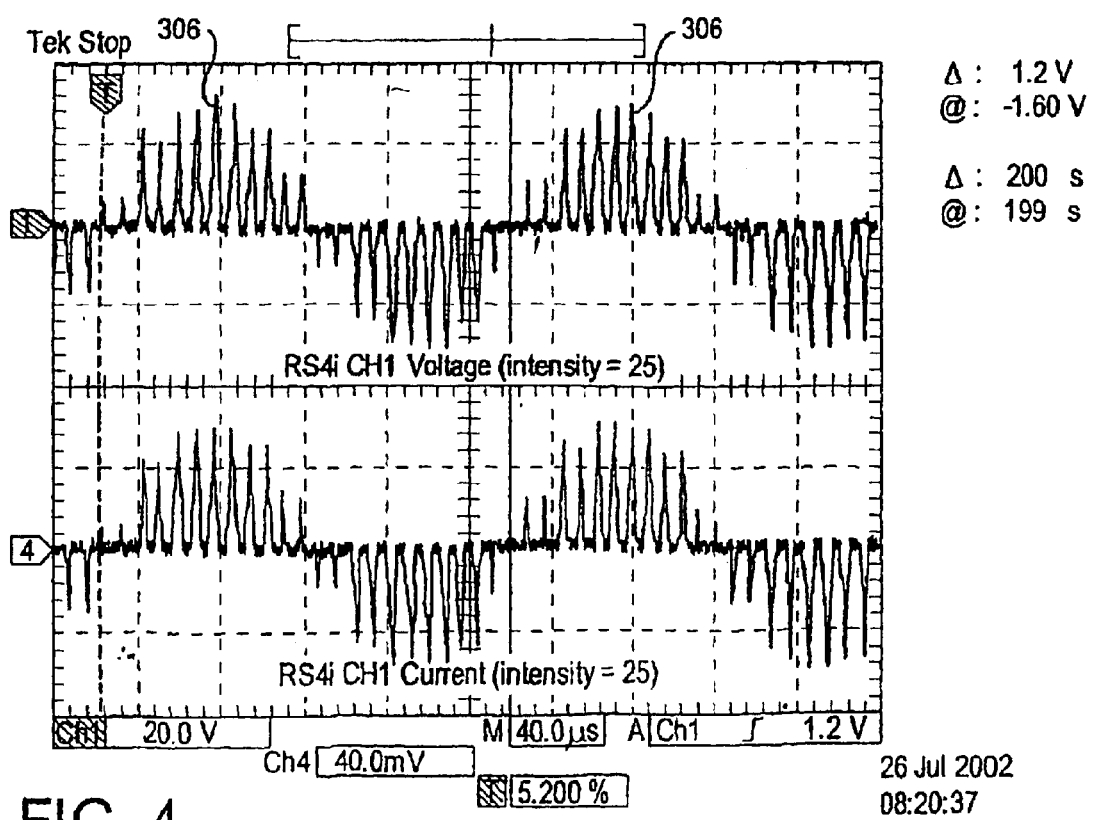
FIG. 4 is a diagram illustrating the DSP generated waveform.

FIG. 4 illustrates the interferential current 306 with the sine-wave-like waveform that is generated by the digital signal processor 102. An example of a suitable commercially available digital signal processor 102 is the RS 4i manufactured by RS Medical of Vancouver, Washington. A field-programmable gate array (not shown) can also be used to shape multiple pulsatile waveforms to approximate the output of a sine-wave generator instead of the digital signal processor 102 described above. The FPGA is an integrated circuit that can be programmed in the field after it is manufactured and allows its user to adjust the circuit output as desired.

In an alternative embodiment, as described above, the digital signal processor may be replaced with the FPGA. Whereas DSP processors typically have only eight dedicated multipliers at their disposal, a higher end FPGA device can offer up to 224 dedicated multipliers plus additional logic element-based multipliers as needed. That allows for complex digital signal processing applications such as finite impulse response filters, forward error correction, modulation-demodulation, encryption and applications such as utilized in the present invention.

Preliminary studies have been conducted by the inventors using the present invention and the results have been summarized by bone growth quantification. The results support the claim that the use of electrical stimulation singly, or in combination with other techniques, augments and enhances healing and effectivenss of biologics for osteogenesis (including but not limited to growth factors, Bone Morphogenetic proteins, Hydroxyapatite, Autogenous Bone Grafts, Human Bone Allografts, Demineralized Bone Matrix (DBM) and systemic use or local application of anti-resorptive drugs (i.e., Foxomax, Raloxifene and others)).

It should be emphasized that the above-described embodiments of the present invention, particularly, any "preferred" embodiments, are merely possible examples of implementations, merely set forth for a clear understanding on the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

We claim:

1. A stimulator for osteogenesis and the treatment of osteoporosis, comprising:
   a pulse generator that generates digital signal pulses;
   a field-programmable gate array connected to said pulse generator that generates a sine-wave-like output waveform that is further processed into first and second circuits; and
   two pairs of surface electrodes connected to said field-programmable gate array and positioned on a subject's skin surface at predetermined locations to produce an interferential current output waveform from said first and second circuits.

2. The stimulator of claim 1, further comprising a means for generating electrical stimulation of bone to enhance healing and effectiveness of biologics for osteogenesis.

3. The stimulator of claim 1, wherein said interferential current output waveform includes a base medium frequency of at least 1 KHz but no more than 20 KHz.

4. The stimulator of claim 1, wherein said interferential current waveform includes a resultant beat frequency of no more than 250 Hz.

5. A method for electrical stimulation of bone to promote osteogenesis, said method comprising:

connecting a pulse generator to a digital signal processor and supplying digital signal pulses to a field-programmable gate array which produces a sine-wave-like current waveform which is further processed and output to first and second pairs of surface electrodes, wherein first and second circuits are created, respectively;

positioning said first pair of surface electrodes on a subject's skin surface at one set of diagonal corners of an incision site;

positioning said second pair of surface electrodes on the subject's skin surface at the other set of diagonal corners of the incision site; and creating an interferential current with a base medium frequency of at least 1 KHz but no more than 20 KHz.

6. The method according to claim 5, wherein said method further includes varying positions of said first and second pairs of surface electrodes.

7. The method according to claim 5, wherein said method further includes modulating outputs of amplitudes of said first and second circuits.

8. The method according to claim 5, wherein said method includes creating an interferential current with a resultant beat frequency of no more than 250 Hz.

9. A method for electrical stimulation of bone to promote osteogenesis, said method comprising:

connecting a pulse generator to a digital signal processor and supplying digital signal pulses to a field-programmable gate array which produces a sine-wave-like current waveform which is further processed and output to first and second pairs of surface electrodes, wherein first and second circuits are created, respectively;

positioning said first pair of surface electrodes on a subject's skin surface at one set of diagonal corners of an incision site;

positioning said second pair of surface electrodes on the subject's skin surface at the other set of diagonal corners of the incision site;

creating an interferential current with a base medium frequency of at least 1 KHz but no more than 20 KHz; and generating electrical stimulation of bone to enhance healing and effectiveness of biologics for osteogenesis.

10. A method of electrical stimulation for osteogenesis and the treatment of osteoporosis, comprising the steps of:

generating digital signal pulses using a pulse generator;

generating a sine-wave-like output waveform from a field-programmable gate array that is connected to said pulse generator;

processing said sine-wave-like output waveform into first and second circuits; and producing an interferential current output waveform from said first and second circuits via two pairs of surface electrodes connected to said field-programmable gate array and positioned at predetermined locations on a subject's skin surface.

* * * * *